US011337830B2

(12) United States Patent
Rodriguez et al.

(10) Patent No.: US 11,337,830 B2
(45) Date of Patent: May 24, 2022

(54) DEFECT GAUGE INSTRUMENT FOR PREPARATION OF SURGICAL SITES

(71) Applicant: Arthrex, Inc., Naples, FL (US)

(72) Inventors: Alexander Emmanuel Rodriguez, Weston, FL (US); John David Paterson, Naples, FL (US); Tyler Clevett, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 333 days.

(21) Appl. No.: 16/568,499

(22) Filed: Sep. 12, 2019

(65) Prior Publication Data

US 2021/0077279 A1  Mar. 18, 2021

(51) Int. Cl.
*A61F 2/46* (2006.01)
*A61B 90/00* (2016.01)
*A61B 17/15* (2006.01)

(52) U.S. Cl.
CPC ............ *A61F 2/4657* (2013.01); *A61B 17/15* (2013.01); *A61B 90/06* (2016.02); *A61B 2090/061* (2016.02); *A61F 2002/4658* (2013.01)

(58) Field of Classification Search
CPC .......................... A61B 90/06–2090/069; A61F 2/4657–2002/4668
See application file for complete search history.

(56) References Cited

U.S. PATENT DOCUMENTS

| 2,975,524 | A  | * | 3/1961  | Field ...................... G01B 5/243 33/534 |
| 4,486,954 | A  | * | 12/1984 | Mock ....................... G01B 3/56 33/533 |
| 5,540,696 | A  | * | 7/1996  | Booth, Jr. ............ A61B 17/154 606/88 |
| 6,712,823 | B2 |   | 3/2004  | Grusin et al. |
| 7,527,631 | B2 |   | 5/2009  | Maroney et al. |
| 8,187,282 | B2 |   | 5/2012  | Tornier et al. |
| 8,414,593 | B2 | * | 4/2013  | Quirno .................. A61F 2/4657 606/90 |
| 8,747,418 | B2 | * | 6/2014  | Qureshi ................. A61B 90/11 606/130 |
| 8,801,725 | B2 | * | 8/2014  | Ritter ..................... A61B 17/17 606/102 |
| 9,615,839 | B2 |   | 4/2017  | Olson |
| 10,433,983 | B1 | * | 10/2019 | Khosla .................... A61B 90/06 |
| 2005/0203532 | A1 | * | 9/2005 | Ferguson ............. A61B 17/025 606/90 |
| 2006/0074353 | A1 |   | 4/2006  | Deffenbaugh et al. |
| 2007/0260260 | A1 | * | 11/2007 | Hahn .................... A61F 2/4657 606/102 |

(Continued)

OTHER PUBLICATIONS

International Search Report & Written Opinion for International Patent Application No. PCT/US2020/050280 completed Dec. 7, 2020.

(Continued)

*Primary Examiner* — Zade Coley
(74) *Attorney, Agent, or Firm* — Carlson, Gaskey & Olds, P.C.

(57) ABSTRACT

This disclosure relates to a defect gauge instrument and method for repairing bone defects. The defect gauge instrument disclosed herein may be utilized to determine one or more characteristics of a bone defect prior to positioning a graft and/or implant at a surgical site.

20 Claims, 8 Drawing Sheets

(56) References Cited

U.S. PATENT DOCUMENTS

| | | | | |
|---|---|---|---|---|
| 2009/0024135 A1* | 1/2009 | Triplett | ............... | A61B 90/94 |
| | | | | 606/102 |
| 2010/0010494 A1* | 1/2010 | Quirno | ............... | A61F 2/4657 |
| | | | | 606/90 |
| 2012/0123426 A1* | 5/2012 | Quirno | ............... | A61F 2/4657 |
| | | | | 606/90 |
| 2014/0107659 A1* | 4/2014 | Walters | ............... | A61F 2/4657 |
| | | | | 606/102 |
| 2018/0280158 A1* | 10/2018 | Murphy | ............... | A61F 2/4657 |

OTHER PUBLICATIONS

International Preliminary Report on Patentability for International Application No. PCT/US2020/050280 dated Mar. 24, 2022.

\* cited by examiner

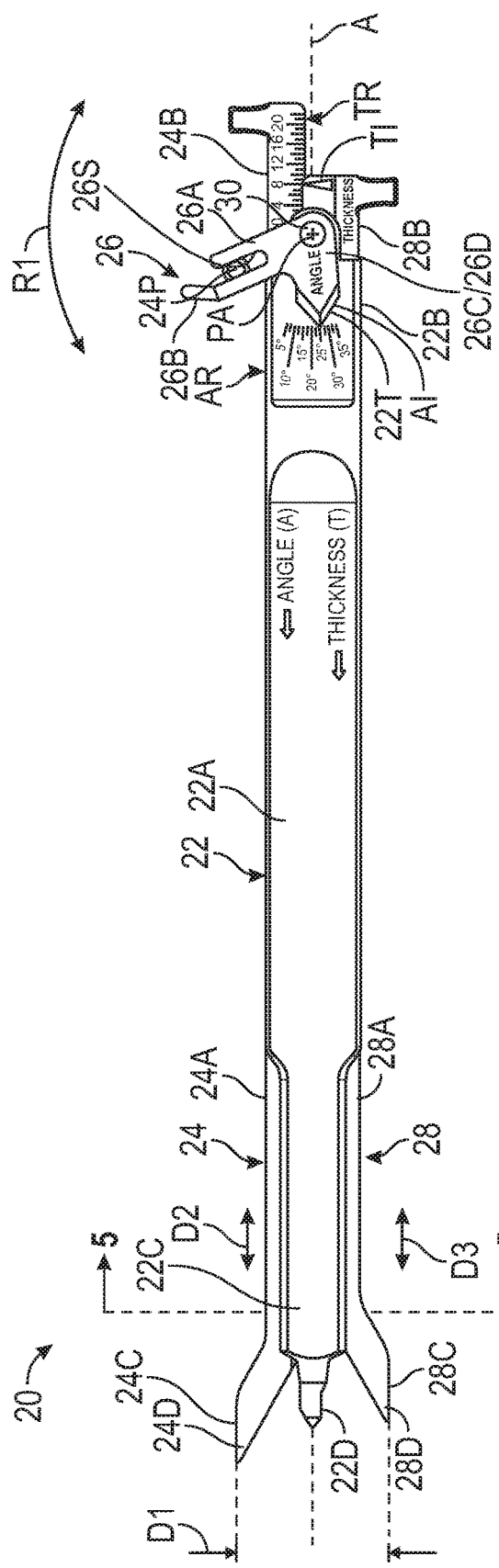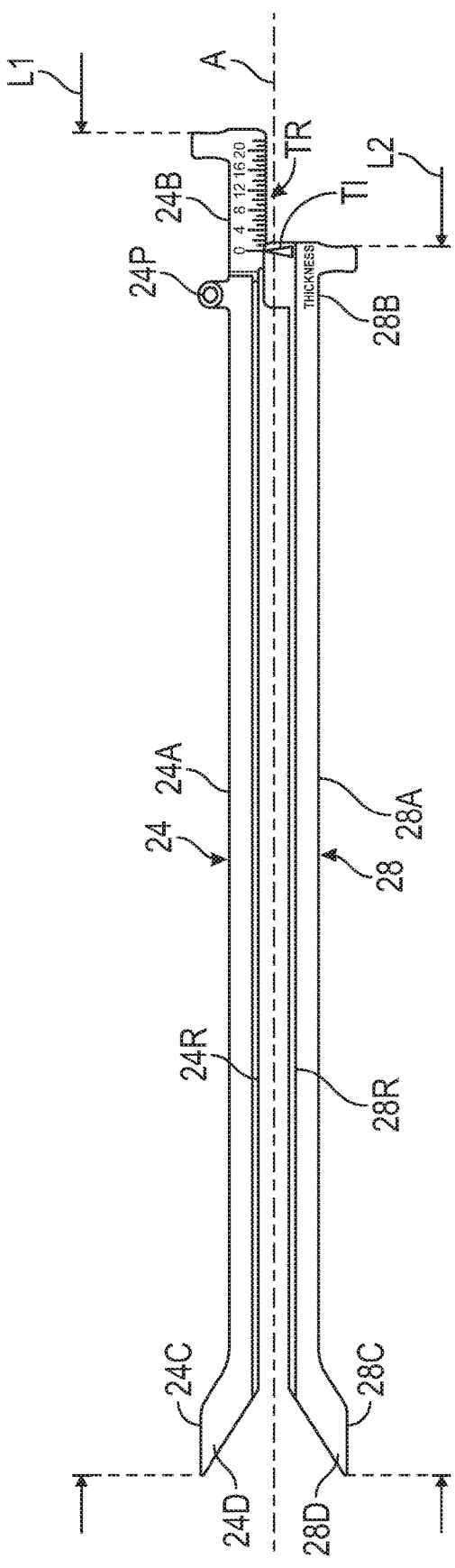

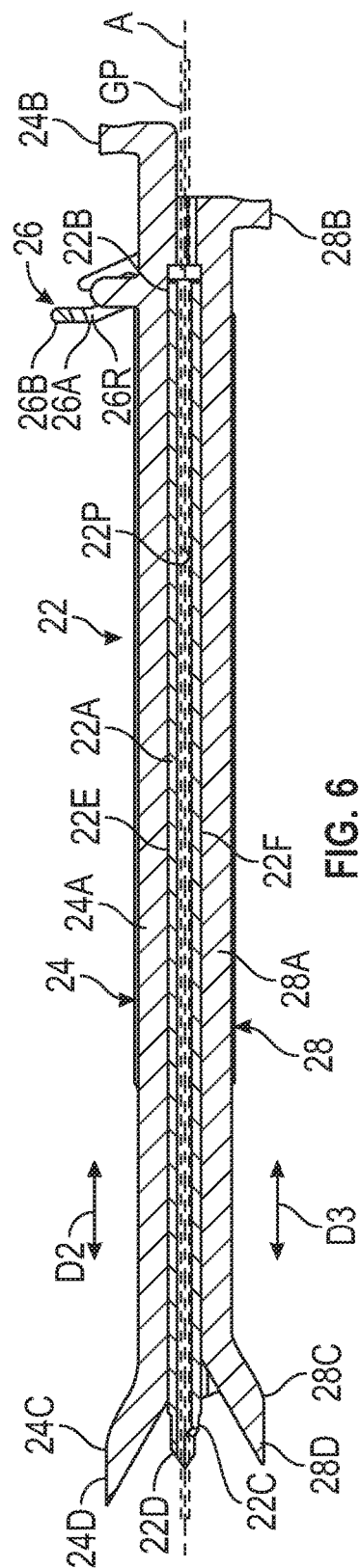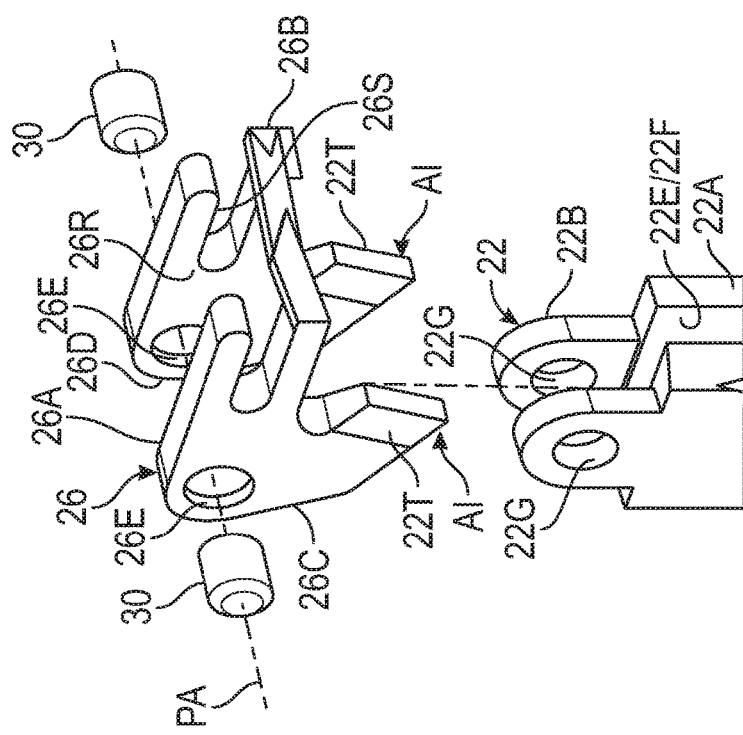
FIG. 6
FIG. 7

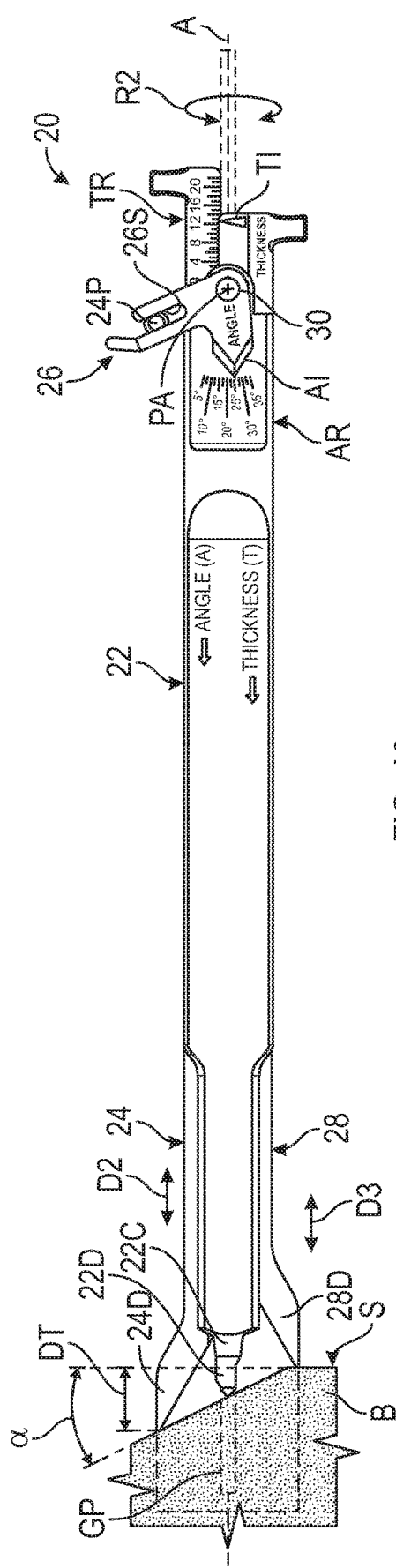
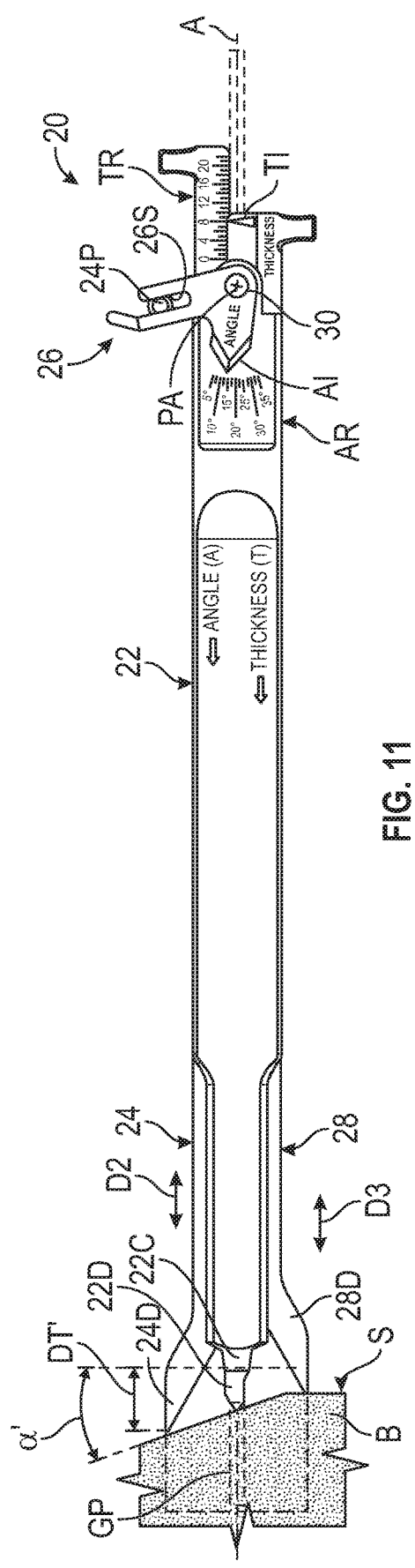
FIG. 10
FIG. 11

DEFECT GAUGE INSTRUMENT FOR PREPARATION OF SURGICAL SITES

BACKGROUND

This disclosure relates to surgical instrumentation and methods for repairing bone defects.

Many bones of the human musculoskeletal system include articular surfaces. The articular surfaces articulate relative to other bones to facilitate different types and degrees of joint movement. The articular surfaces can erode (i.e., experience bone loss) over time due to repeated use or wear or can fracture as a result of a traumatic impact. These types of bone defects can cause joint instability and pain.

Bone deficiencies may occur along the articular surfaces of the glenoid bone. Some techniques utilize a bone graft to fill a defect in the bone. The graft can be dimensioned to approximate a size of the defect.

SUMMARY

This disclosure relates to a surgical instrument and method. The surgical instrument may be used during methods for repairing bone defects. The surgical instrument described herein may be utilized to evaluate or determine one or more characteristics of a bone defect at a surgical site, such as a retroversion angle and thickness of the bone defect.

A defect gauge instrument for evaluating a surgical site according to an embodiment of the present disclosure includes, inter alia, a housing extending along a longitudinal axis between proximal and distal end portions, the housing defining a first channel extending at least partially between the proximal and distal end portions, an angle indicator aligned with an angular ruler, and an angle leg at least partially received in the first channel such that relative movement between the angle leg and the housing causes relative movement between the angle indicator and the angular ruler.

A defect gauge instrument for evaluating a surgical site according to an embodiment of the present disclosure includes, inter alia, a housing extending along a longitudinal axis between proximal and distal end portions, angle and thickness legs coupled to the housing, the angle and thickness legs dimensioned to contact bone adjacent the distal end portion, an angle indicator aligned with an angular ruler, a thickness indicator aligned with a thickness ruler, and an angle arm pivotably attached to the housing. Relative movement between the angle leg and the housing causes relative movement between the angle indicator and the angular ruler, and relative movement between the thickness leg and the housing causes relative movement between the thickness indicator and the thickness ruler.

A method of use for a defect gauge instrument for evaluating a surgical site according to an embodiment of the present disclosure includes, inter alia, moving a housing along a guide pin such that a distal end portion of the housing contacts bone, and measuring a retroversion angle of a defect in the bone, including causing relative movement between an angle indicator and an angular ruler in response to relative movement between an angle leg and the housing such that the angle leg contacts the bone.

BRIEF DESCRIPTION OF THE DRAWINGS

FIG. 2 illustrates a side view of the instrument of FIG. 1.

FIG. 3 illustrates a side view of an angle leg and a thickness leg of the instrument of FIG. 1.

FIG. 6 illustrates a sectional view taken along a longitudinal axis of the instrument of FIG. 2.

FIG. 7 illustrates an exploded perspective view of an angle arm and the housing of FIG. 2.

FIG. 10 illustrates the instrument situated at a position at the surgical site of FIG. 9.

FIG. 11 illustrates the instrument situated at another position at the surgical site of FIG. 9.

DETAILED DESCRIPTION

Figure 1:
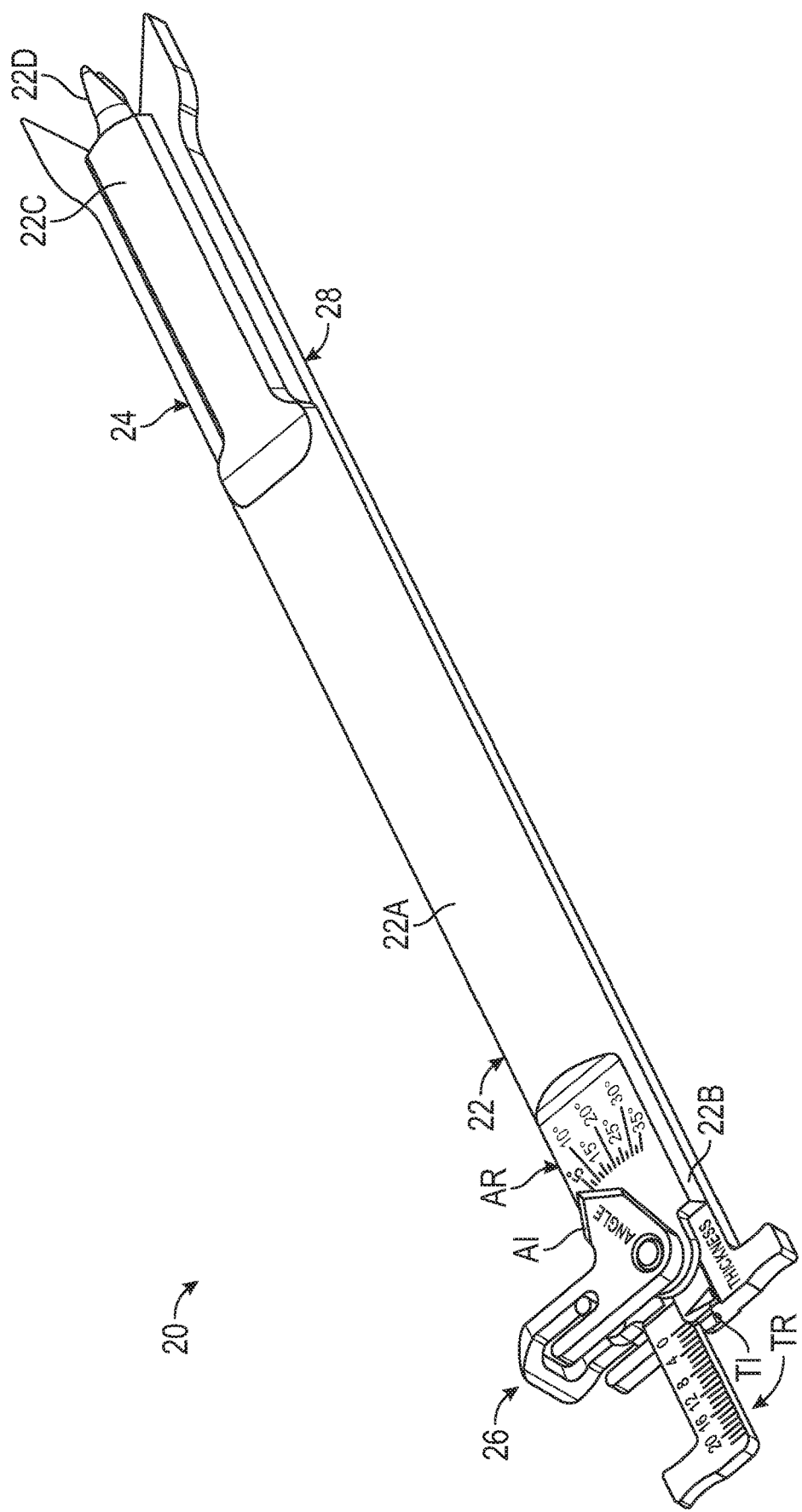
FIG. 1 illustrates a perspective view of an exemplary defect gauge instrument for evaluating a surgical site.

This disclosure relates to a surgical device and method for evaluating or determining one or more characteristics of a surgical site. The device described herein may be utilized in preparation of the surgical site, such as dimensioning a graft according to a measured retroversion angle and/or thickness of a defect in bone at the surgical site.

A defect gauge instrument for evaluating a surgical site according to an embodiment of the present disclosure includes, inter alia, a housing extending along a longitudinal axis between proximal and distal end portions, the housing defining a first channel extending at least partially between the proximal and distal end portions, an angle indicator aligned with an angular ruler, and an angle leg at least partially received in the first channel such that relative movement between the angle leg and the housing causes relative movement between the angle indicator and the angular ruler.

In a further embodiment, an angle arm is pivotably attached to the housing, the angle arm defining the angle indicator, and an actuation pin extends outwardly from the angle leg. The angle arm defines a slot dimensioned to at least partially receive the actuation pin, and the actuation pin is dimensioned to move along a length of the slot in response to movement of the angle leg relative to the housing to cause the angle arm to pivot.

In a further embodiment, the housing defines the angular ruler, and the angle arm includes a tapered portion defining the angle indicator.

In a further embodiment, the housing defines a passageway extending along the longitudinal axis between the proximal and distal end portions, and the passageway is dimensioned to slidably receive a guide pin.

In a further embodiment, the housing defines a second channel extending at least partially between the proximal and distal end portions. A thickness leg at least is partially received in the second channel such relative movement between the thickness leg and the housing causes relative movement between a thickness indicator and a thickness ruler.

In a further embodiment, the angle leg defines the thickness ruler, and the thickness leg defines the thickness indicator.

In a further embodiment, the angle and thickness legs have respective guide rails slidably received in the respective first and second channels, and the first and second channels are dimensioned to mate with the guide rails to limit radial movement of the angle and thickness legs relative to the longitudinal axis.

In a further embodiment, an angle arm is pivotably attached to the housing, the angle arm defining the angle indicator, and an actuation pin extends outwardly from the angle leg. The angle arm defines a slot dimensioned to at least partially receive the actuation pin, and the actuation pin is dimensioned to move along a length of the slot in response to movement of the angle leg relative to the housing to cause the angle arm to pivot.

In a further embodiment, an external surface of the housing defines the angular ruler, and the angle arm includes a tapered portion defining the angle indicator.

In a further embodiment, the angle arm includes a main body having a generally U-shaped geometry, the slot is defined in the main body, the main body defines a recess dimensioned to at least partially receive the proximal end portion of the housing, and the tapered portion extends outwardly from an end portion of the main body. The end portion of the angle arm is pivotably attached to the proximal end portion of the housing at a retention pin.

In a further embodiment, the angle leg is dimensioned to extend a first length relative to the longitudinal axis, the thickness leg is dimensioned to extend a second length relative to the longitudinal axis, and the first length is greater than the second length.

In a further embodiment, the distal end portion of the housing defines a tapered engagement portion dimensioned to contact bone, the housing defines a passageway extending along the longitudinal axis between the tapered engagement portion and the proximal end portion, and the passageway is dimensioned to slidably receive a guide pin.

In a further embodiment, the angle leg tapers to a first tip portion, the thickness leg tapers to a second tip portion, and the first and second tip portions are dimensioned to contact bone on opposed sides of the tapered engagement portion.

A defect gauge instrument for evaluating a surgical site according to an embodiment of the present disclosure includes, inter alia, a housing extending along a longitudinal axis between proximal and distal end portions, angle and thickness legs coupled to the housing, the angle and thickness legs dimensioned to contact bone adjacent the distal end portion, an angle indicator aligned with an angular ruler, a thickness indicator aligned with a thickness ruler, and an angle arm pivotably attached to the housing. Relative movement between the angle leg and the housing causes relative movement between the angle indicator and the angular ruler, and relative movement between the thickness leg and the housing causes relative movement between the thickness indicator and the thickness ruler.

In a further embodiment, the housing defines the angular ruler and the angle arm defines the angle indicator such that axial movement of the angle leg relative to the longitudinal axis causes the angle indicator to pivot relative to the angular ruler, and the angle leg defines the thickness ruler and the thickness leg defines the thickness indicator such that axial movement of the thickness leg relative to the longitudinal axis causes the thickness indicator to move relative to the thickness ruler.

In a further embodiment, the housing defines a passageway dimensioned to slidably receive a guide pin between the angle and thickness legs.

A method of use for a defect gauge instrument for evaluating a surgical site according to an embodiment of the present disclosure includes, inter alia, moving a housing along a guide pin such that a distal end portion of the housing contacts bone, and measuring a retroversion angle of a defect in the bone, including causing relative movement between an angle indicator and an angular ruler in response to relative movement between an angle leg and the housing such that the angle leg contacts the bone.

In a further embodiment, the method includes measuring a thickness of the defect in the bone, including causing relative movement between a thickness indicator and a thickness ruler in response to relative movement between a thickness leg and the housing such that the thickness leg contacts the bone.

In a further embodiment, the step of measuring the retroversion angle includes causing the angle arm to pivot in response to axial movement of the angle leg relative to a longitudinal axis of the housing. The method includes rotating the housing about the guide pin from a first position to a second, different position subsequent to the steps of measuring the retroversion angle of the defect and measuring the thickness of the defect when the housing is in the first position, and repeating the steps of measuring the retroversion angle of the defect and measuring the thickness of the defect when the housing in the second position.

In a further embodiment, the method includes selecting a maximum value of the retroversion angle with respect to the first and second positions, and selecting a maximum value of the thickness with respect to the first and second positions.

FIGS. 1-2 illustrate an exemplary defect gauge instrument 20 that can be utilized to evaluate various characteristics of a defect at a surgical site. The instrument 20 includes a shaft or housing 22 that having an elongated main body 22A that extends along a longitudinal axis A (FIG. 2) between a proximal end portion 22B and a distal end portion 22C. The distal end portion 22C defines a tapered engagement portion 22D that is dimensioned to contact bone.

The instrument 20 includes an angle foot or leg 24 coupled to an angle arm 26. The instrument 20 includes a thickness foot or leg 28 opposed to the angle leg 24. The angle leg 24 and thickness leg 28 are coupled to the housing 22 on opposed sides of the longitudinal axis A. The instrument 20 can be substantially symmetrical relative to a reference plane REF (FIG. 5) that extends along the longitudinal axis A. The instrument 20 includes an angle indicator AI aligned with an angular ruler AR to measure a retroversion angle of a defect in bone, and includes a thickness indicator TI moveable relative to a thickness ruler TR to measure a depth or thickness of the defect in bone, as discussed in more detail below. In the illustrative embodiment of FIG. 1, an external surface along the proximal end portion 22B of the housing 22 defines the angular ruler AR, the angle arm 26 defines the angle indicator AI, the angle leg 24 defines the thickness ruler TR, and the thickness leg 28 defines the thickness indicator TI. Of course, an opposite configuration is also contemplated in which the angle arm 26 defines the angular ruler AR and the housing 22 defines the angle indicator AI, and/or the thickness leg 28 defines the thickness ruler TR and the angle leg 24 defines the thickness indicator TI. In other embodiments, one of the thickness ruler TR or thickness indicator TI is defined along the housing 22 and another one of the thickness ruler TR or thickness indicator TI is defined along the thickness leg 28.

Referring to FIGS. 2-3, the angle leg 24 includes an elongated body 24A extending between a proximal end portion 24B and a distal end portion 24C. The thickness leg 28 includes an elongated body 28A extending between a proximal end portion 28B and a distal end portion 28C. The proximal end portion 24B of the angle leg 24 can define the thickness ruler TR. The proximal end portion 28B of the thickness leg 28 can define the thickness indicator TI. Each of the legs 24, 28 includes one or more guide rails 24R, 28R (FIG. 3) for securing the legs 24, 28 to the housing 22.

The legs 24, 28 are dimensioned to contact bone adjacent to the distal end portion 22C of the housing 22. In the illustrated example of FIGS. 2-3, the angle leg 24 tapers to a first tip portion 24D along the distal end portion 24C, and the thickness leg 28 tapers to a second tip portion 28D adjacent the distal end portion 28C of the thickness leg 28. The first and second tip portions 24D, 28D are dimensioned to contact bone on opposed sides of the tapered engagement portion 22D of the housing 22.

The angle leg and thickness legs 24, 28 can be dimensioned such that the tip portions 24D, 28D are spaced apart by a distance D1 (FIG. 2). The distance D1 is defined with respect to the distal most point of the tip portions 24D, 28D. The distance D1 can correspond to a width of an implant or graft selected by the surgeon to be situated at a surgical site. In an embodiment, the distance D1 is approximately 25 mm. In another embodiment, the distance D1 is approximately 30 mm. It should be appreciated that the distance D1 can be different than 25 mm or 30 mm in accordance with the teachings disclosed herein. For the purposes of this disclosure, the term "approximately" means ±3% of the disclosed value unless otherwise stated.

Referring to FIG. 3, with continuing reference to FIGS. 1-2, the angle and thickness legs 24, 28 can be dimensioned to extend different lengths relative to the longitudinal axis A. The angle leg 24 extends at least a first length L1, and the thickness leg 28 extends a second length L2 relative to the longitudinal axis A. The first and second lengths L1, L1 can be substantially the same or can differ. In the illustrative example of FIG. 3, the first length L1 is greater than the second length L2. The first length L1 is defined as the distance between the distal most point of the angle leg 24 and the proximal most point of the thickness ruler TR. The second length L2 is defined by a distal most point of the thickness leg 28 and a terminal end of the thickness indicator TI. In other embodiments, the first length L1 is a maximum length of the angle leg 24, and the second length L2 is a maximum length of the thickness leg 28.

Figure 4:
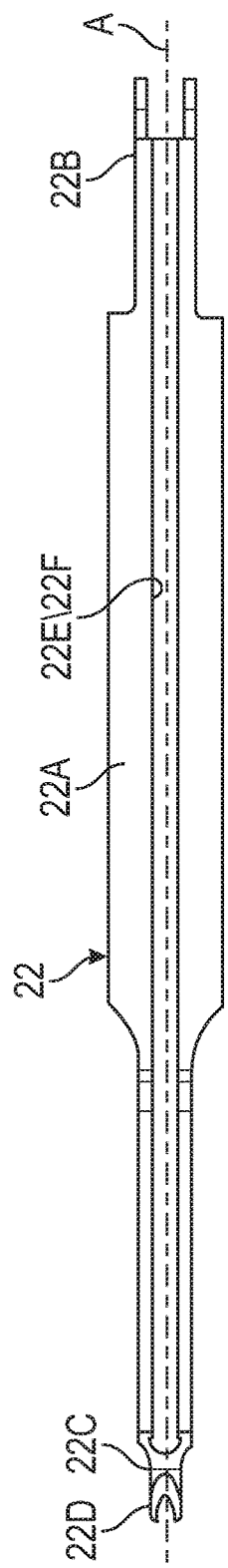
FIG. 4 illustrates a side view of a housing of the instrument of FIG. 1.
Figure 5:
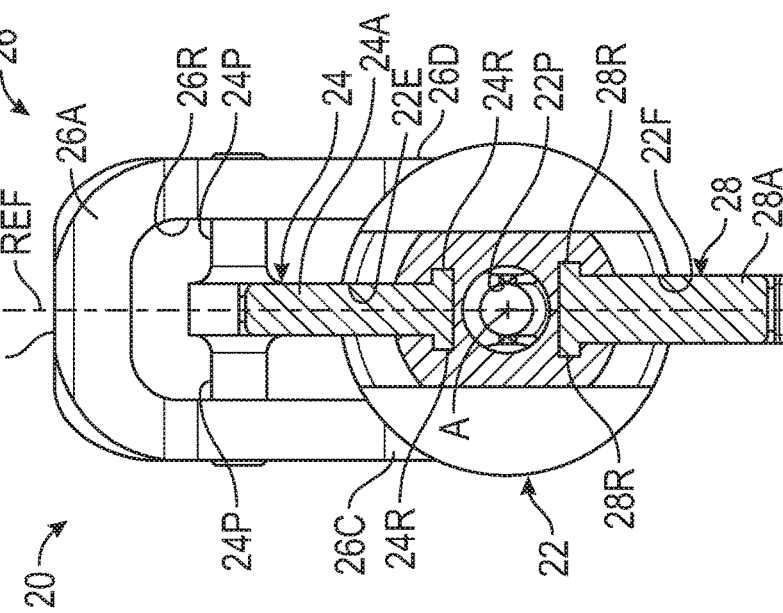
FIG. 5 illustrates a sectional view of the instrument taken along line 5-5 of FIG. 2.

Referring to FIGS. 4-5, with continuing reference to FIGS. 2-3, the housing 22 defines first and second channels 22E, 22F each extending at least partially between the proximal and distal end portions 22B, 22C of the housing 22. In the illustrated example of FIG. 4, each of the channels 22E, 22F extends at least a majority of a length of the housing 22 with respect to the longitudinal axis A.

Referring to FIGS. 5-6, with continuing reference to FIGS. 2-3, the angle and thickness legs 24, 28 can include opposed pairs of guide rails 24R, 28R extending outwardly from opposed sides of the respective body 24A, 28A. The legs 24, 28 can have a generally T-shaped cross-sectional geometry along the respective rails 24R, 28R. The channels 22E, 22F can have a generally T-shaped cross-sectional geometry are dimensioned to mate with the rails 24R, 28R to limit radial movement of the legs 24, 28 relative to the longitudinal axis A. The angle leg 24 is dimensioned to be at least partially slidably received in the first channel 22E, and the thickness leg 28 is dimensioned to be at least partially slidably received in the second channel 22F.

The housing 22 defines a passageway 22P extending along the longitudinal axis A between proximal and distal end portions 22B, 22C. The passageway 22P can extend along the longitudinal axis A between the tapered engagement portion 22D and the proximal end portion 22B of the housing 22. The passageway 22P is dimensioned to slidably receive a guide pin GP (shown in dashed lines in FIG. 6 for illustrative purposes) between the legs 24, 28.

Referring to FIGS. 5 and 7, with continuing reference to FIGS. 2 and 6, the angle arm 26 includes a main body 26A having a generally U-shaped geometry to define a recess 26R. The recess 26R is dimensioned to at least partially receive the proximal end portion 22B of the housing 22, as illustrated by FIGS. 5-6 (see also FIG. 2). The main body 26A includes a bridge 26B that extends between opposed end portions 26C, 26D. The angle arm 26 includes a pair of tapered portions 22T (FIGS. 2 and 7) extending outwardly from the respective end portions 26C, 26D. Each tapered portion 22T can be dimensioned to generally taper to a respective point to define a respective angle indicator AI.

Each of the end portions 26C, 26D of the angle arm 26 is pivotably attached to the proximal end portion 22B of the housing 22 at one or more fasteners or retention pins 30 (FIGS. 2 and 7). The opposed end portions 26C, 26B define respective apertures 26E (FIG. 7) dimensioned to receive the retention pins 30. Each retention pin 30 is dimensioned to extend at least partially into a respective aperture 22G (FIG. 7) defined in the proximal end portion 22B of the housing 22. The retention pins 30 are fixedly attached to the proximal end portion 22B such that the angle arm 26 is pivotably attached to the housing 22, as illustrated in FIG. 2. The retention pins 30 establish the pivot axis PA.

The main body 26A of the angle arm 26 defines a groove or slot 26S (FIGS. 2 and 7). The angle leg 24 includes at least one or an opposed pair of actuation pins 24P that extend outwardly from opposed sides of the main body 24A, as illustrated in FIG. 5 (see also FIGS. 2-3). The slot 26S is dimensioned to at least partially receive each of the actuation pins 24P, as illustrated in FIG. 2. Each of the actuation pins 24P is dimensioned to translate or otherwise move along a length of the slot 26S in response to movement of the angle leg 24 in a direction D2 (FIGS. 2 and 6) relative to the housing 22 to cause the angle arm 26 to pivot about the pivot axis PA in the direction R1 (FIG. 2).

Referring back to FIG. 2, the legs 24, 28 and angle arm 26 are moveable relative to the housing 22 to determine one or more characteristics of a bone defect at a surgical site. The angle arm 26 is rotatable in a direction R1 about the pivot axis PA to align the angle indicator AI with a selected value along a range of angles along the angular ruler AR. Relative movement between the angle leg 24 and the housing 22 causes relative movement between the angle indicator AI and the angular ruler AR. In the illustrative embodiment of FIGS. 2 and 6, translation or axial movement of the angle leg 24 in the direction D2 along the respective channel 22E and relative to the longitudinal axis A causes the angle indicator AI to pivot or otherwise move relative to the angular ruler AR in response to pivoting or otherwise moving the angle arm 26 to select one of the values along the angular ruler AR.

The angular ruler AR can correspond to a range of retroversion angles of a defect at a surgical site. The angular ruler AR can define a range of values between approximately 5 degrees and approximately 35 degrees in 2.5 degree increments as illustrated in FIG. 2, for example. It should be appreciated that a minimum angle of the angular ruler AR can be greater than 0 degrees, such as approximately 5 or 10 degrees, and a maximum angle of the angular ruler AR can be lesser or greater than 35 degrees, such as approximately 25 or 45 degrees. In the illustrated example of FIG. 2, the angular indicator AI is aligned with a selected value of approximately 25 degrees along the angular ruler AR.

Relative movement between the thickness leg 28 and the angle leg 24 and/or housing 22 causes relative movement between the thickness indicator TI and the thickness ruler TR. The thickness indicator TI is aligned with a selected position along the thickness ruler TR in response to translating or otherwise moving the thickness leg 28 relative to the angle leg 24. In the illustrative embodiment of FIGS. 2 and 6, the thickness leg 28 is at least partially received in the respective channel 22F such that translation or axial movement of the thickness leg 28 in a direction D3 in the channel 22F causes the thickness indicator TI to move relative to the thickness ruler TR.

The thickness ruler TR can correspond to a range of depths or thicknesses of a defect at a surgical site. The thickness ruler TR can range between approximately 0 mm and approximately 22 mm in 1 mm increments as illustrated in FIGS. 2-3, for example. It should be appreciated that a minimum thickness of the thickness ruler TR can be greater than 0 mm, such as approximately 5 or 10 mm, and a maximum thickness of the thickness ruler TR can be lesser or greater than 22 mm, such as approximately 15 or 25 mm.

Figure 8:
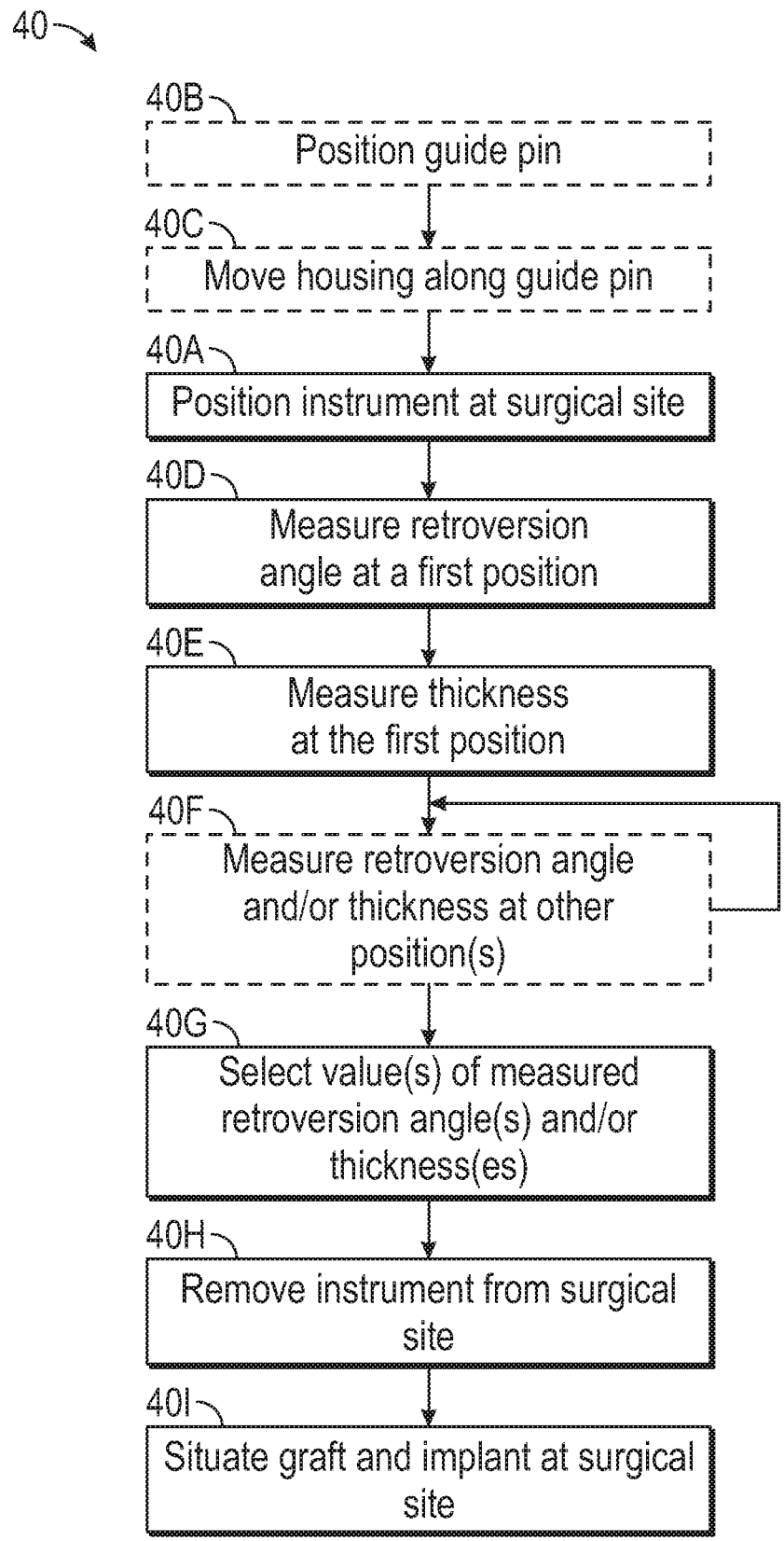
FIG. 8 illustrates an exemplary method for evaluating a surgical site.

An exemplary method of using the instrument 20 will now be described. Referring to FIG. 8, an exemplary method in a flowchart 40 for evaluating a surgical site is shown. Reference is made to the instrument 20 of FIGS. 9-11 for illustrative purposes. The method 40 can be utilized to evaluate various characteristics at a surgical site, such as a retroversion angle and/or a thickness of a defect in bone. Fewer or additional steps than are recited below could be performed within the scope of this disclosure, and the recited order of steps is not intended to limit this disclosure.

Figure 9:
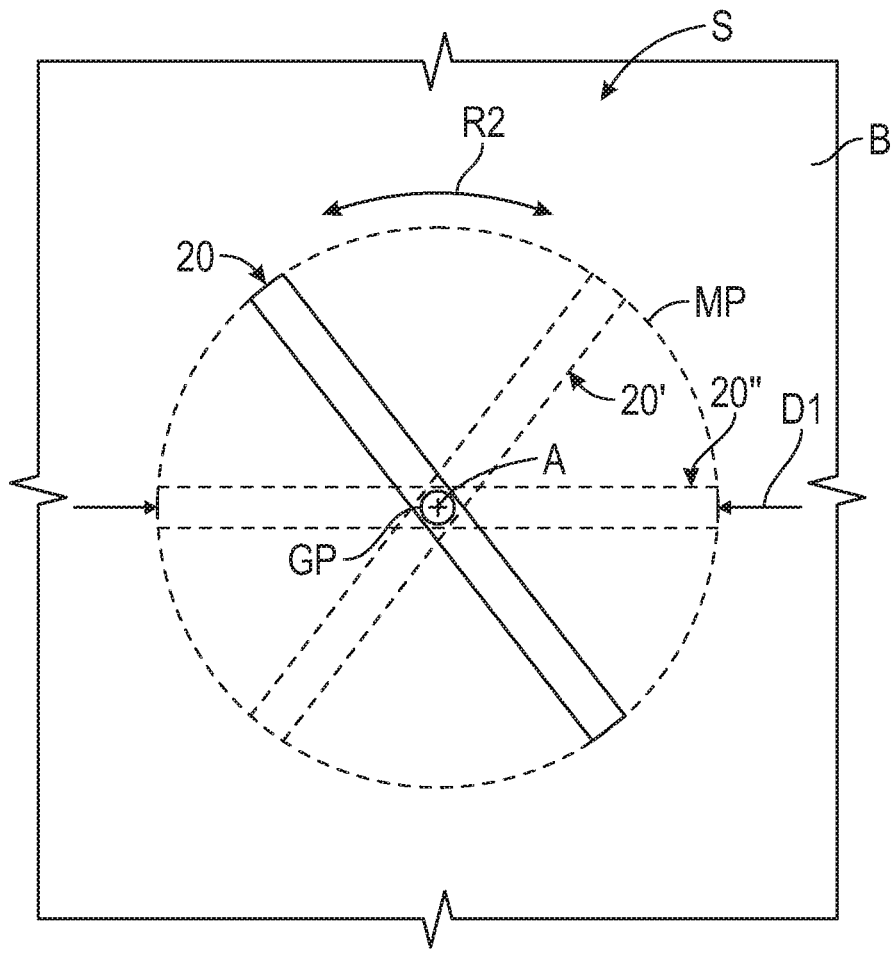
FIG. 9 illustrates the instrument situated at a plurality of positions at a surgical site.

Referring to FIGS. 8-9, at step 40A the instrument 20 is positioned at a surgical site S. In an embodiment, the surgical site S is an articulating surface of a glenoid of a shoulder joint. However, the method could be performed to evaluate defects in various other tissue within the scope of this disclosure. In other words, this disclosure is in no way limited to evaluating bone defects of the glenoid.

Step 40A can include positioning a guide pin GP in bone B at the surgical site B at step 40B such that the guide pin GP is coaxial with the longitudinal axis A. Step 40A can include moving the housing 22 along a guide pin GP such that the tapered engagement portion 22D of the housing 22 contacts the bone B at step 40C, as illustrated in FIGS. 10-11.

The instrument 20 can be moved by the surgeon to evaluate various characteristics of a defect at various locations along the surgical site S. The housing 22 is rotatable in a direction R2 about the guide pin GP and longitudinal axis A between a plurality of positions along a measurement path MP (shown in dashed lines in FIG. 9 for illustrative purposes). The instrument 20 is schematically illustrated in FIG. 8 at three example positions (indicated at 20, 20', and 20"). The measurement path P can correspond to the distance D1 (FIG. 2) between the tip portions 24D, 28D of the legs 24, 28. FIGS. 10-11 illustrate the instrument 20 situated at two different rotational positions (e.g., first and second positions) relative to the guide pin GP and longitudinal axis A, which may correspond to the positions of instruments 20, 20' in FIG. 9, for example.

Referring to FIG. 10, with continuing reference to FIG. 8, at step 40D the surgeon measures a retroversion angle α of a defect in the bone B at a first position. Step 40D can include causing relative movement between the angle indicator AI and the angular ruler AR in response to relative movement between the angle leg 24 and the housing 22 such that the angle leg 24 contacts the bone. In embodiments, step 40D includes causing the angle indicator AI to move along the angular ruler AR in response to moving the angle leg 24 relative to the housing 22 such that the angle leg 24 contacts the bone B at a position along the measurement path P (FIG. 9). Step 40D can include causing the angle arm 26 to pivot in response to axial movement of the angle leg 24 relative to the longitudinal axis A. In the illustrative embodiment of FIG. 10, the angle indicator AI indicates that the retroversion angle α at the first position is approximately 25 degrees.

At step 40E, the surgeon measures a thickness DT of the defect in the bone B. The thickness DT can correspond to a thickness of a graft or portion of an implant (e.g., augment) to be situated at the surgical site S. Step 40E can include causing relative movement between the thickness indicator TI and the thickness ruler TR in response to relative movement between the thickness leg 28 and the housing 22 and/or angle leg 24 such that the thickness leg 28 contacts the bone. In embodiments, step 40E includes causing the thickness indicator TI to move relative to the thickness ruler TR in response to moving the thickness leg 28 relative to the housing 22 such that the leg 28 contacts the bone B at a position along the measurement path P (FIG. 9). In the illustrative embodiment of FIG. 10, the thickness indicator TI indicates that the thickness DT at the first position is approximately 12 mm.

The retroversion angle α and/or thickness DT of the defect can be measured by the surgeon at one or more other positions relative to the measurement path P (FIG. 9) at step 40F. Step 40F can include rotating the housing 22 about the guide pin GP in the direction R2 from the first position to a second, different position subsequent to measuring the retroversion angle α and/or thickness DT at steps 40D and/or 40E. Step 40F can include repeating steps 40D and/or 40E when the housing 22 is situated at the one or more other positions. FIG. 11 illustrates the instrument 20 situated at a second position. The legs 24, 28 contact the bone B at a different position along the measurement path P (FIG. 9) than illustrated by the position of the instrument 20 in FIG. 10. In the illustrative embodiment of FIG. 11, the angle indicator AI indicates that the retroversion angle α' is approximately 15 degrees, and the thickness indicator TI indicates the thickness DT' is approximately 7 mm.

At step 40G, the surgeon can select one or more values of the measured retroversion angle(s) α and/or thickness(es) DT determined at steps 40D-40F. Step 40G can include selecting a maximum value of the measured retroversion angle α and/or a maximum value of the measured thickness DT with respect to the plurality of positions, such as the positions of the instrument 20 in FIGS. 10-11. The selected values can approximate a profile of a defect in the glenoid, which can be characterized by the Walch Classification. At step 40H the instrument 20 is removed from the surgical site S.

Figure 12:
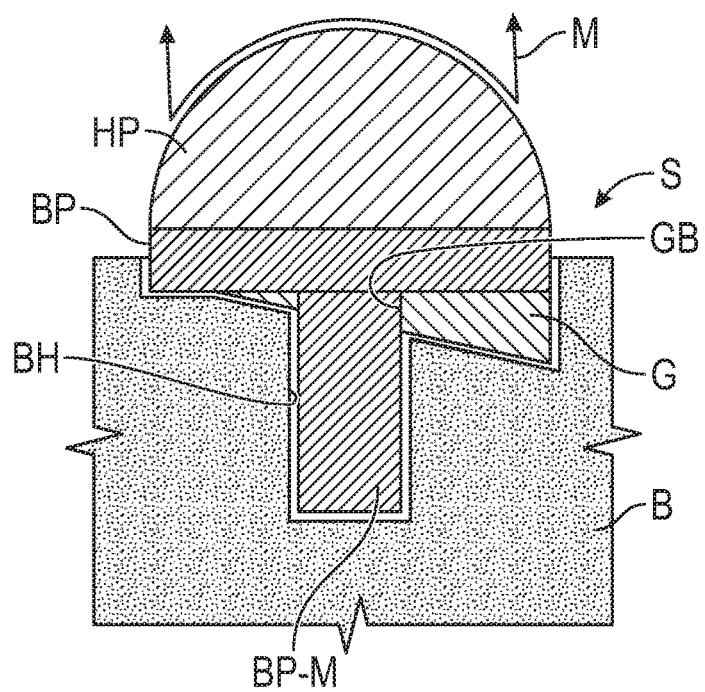
FIG. 12 schematically illustrates a graft positioned at a surgical site.
Figure 13:
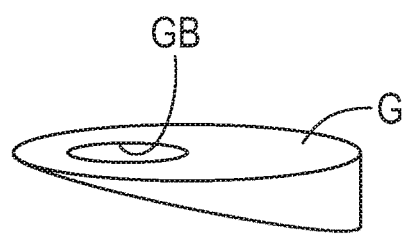
FIG. 13 illustrates an isolated perspective view of the graft of FIG. 12.

Referring to FIG. 12, with continuing reference to FIG. 8, at step 40I the surgeon can position a graft G (see also FIG. 13) at the surgical site S. A geometry of the graft G can be defined according to measured value(s) selected at step 40G, such as the maximum values of the measured retroversion angle α and/or measured thickness DT.

Step 40I can include placing or otherwise securing the graft G to an implant such as a bone plate BP. The graft G is oriented relative to the defect. The bone plate BP can include an anchoring member BP-M that is dimensioned to extend through an inner bore GB of the graft G to secure the bone plate BP at the surgical site S. The graft G is dimensioned to extend along a backside of the bone plate BP such that at least a portion of the graft G is spaced apart from a sidewall of the bone plate BP, as illustrated in FIG. 12.

The surgical site S may be prepared for receiving the graft G and at least a portion of the bone plate BP. This may include forming at least one recess or hole BH in bone B at the surgical site S. The hole BH may be formed to remove tissue from a defect in the bone B. The hole BH can be dimensioned to at least partially receive the bone plate BP and graft G. The hole BH may be drilled, punched, reamed, tapped, or otherwise formed. The surgeon can repeat steps 40D, 40E and/or 40F to reassess the retroversion angle α and thickness DT after formation of the hole BH and prior to dimensioning the graft G. The bone plate BP can be situated at surgical site S such that the backside of the bone plate BP abuts against surfaces of the bone hole BH.

A head portion or glenosphere HP can be secured to the bone plate BP to provide an articulating surface for mating with an opposed articulating member M. The articulating member M can be an implant secured to the humerus, for example. In other embodiments, the bone plate BP provides the articulating surface.

The novel device and method of this disclosure provide versatility in evaluating a defect at a surgical site, including more closely approximating a contour of a bone surface, such as a bone void. Measurements with the disclosed instrument can be utilized to more closely dimension a graft and/or implant, which can lead to improved healing at the surgical site.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A defect gauge instrument for evaluating a surgical site comprising:
   a housing extending along a longitudinal axis between proximal and distal end portions, the housing defining a first channel extending at least partially between the proximal and distal end portions;
   an angle indicator aligned with an angular ruler;
   an angle leg at least partially received in the first channel such that relative movement between the angle leg and the housing causes relative movement between the angle indicator and the angular ruler;
   an angle arm pivotably attached to the housing, the angle arm defining the angle indicator; and
   an actuation pin extending outwardly from the angle leg, wherein the angle arm defines a slot dimensioned to at least partially receive the actuation pin, and the actuation pin is dimensioned to move along a length of the slot in response to movement of the angle leg relative to the housing to cause the angle arm to pivot.

2. The instrument as recited in claim 1, wherein the housing defines the angular ruler, and the angle arm includes a tapered portion defining the angle indicator.

3. The instrument as recited in claim 1, wherein the housing defines a passageway extending along the longitudinal axis between the proximal and distal end portions, and the passageway is dimensioned to slidably receive a guide pin.

4. The instrument as recited in claim 1, wherein:
   a terminal end of the angle leg is dimensioned to extend outwardly from the distal end portion of the housing to cause the angle arm to pivot.

5. The instrument as recited in claim 4, wherein:
   the angle leg includes an elongated leg body and a pair of guide rails that extend outwardly from opposite sides of the leg body; and
   the first channel extends along a sidewall of the housing between the proximal and distal end portions, and the first channel has a T-shaped cross-sectional geometry that is dimensioned to mate with the leg body and the pair of guide rails.

6. A defect gauge instrument for evaluating a surgical site comprising:
   a housing extending along a longitudinal axis between proximal and distal end portions, the housing defining a first channel extending at least partially between the proximal and distal end portions, and the housing defining a second channel extending at least partially between the proximal and distal end portions;
   an angle indicator aligned with an angular ruler;
   an angle leg at least partially received in the first channel such that relative movement between the angle leg and the housing causes relative movement between the angle indicator and the angular ruler; and
   a thickness leg at least partially received in the second channel such relative movement between the thickness leg and the housing causes relative movement between a thickness indicator and a thickness ruler.

7. The instrument as recited in claim 6, wherein the angle leg defines the thickness ruler, and the thickness leg defines the thickness indicator.

8. The instrument as recited in claim 6, wherein the angle and thickness legs have respective guide rails slidably received in the respective first and second channels, and the first and second channels are dimensioned to mate with the guide rails to limit radial movement of the angle and thickness legs relative to the longitudinal axis.

9. The instrument as recited in claim 6, further comprising:
   an angle arm pivotably attached to the housing, the angle arm defining the angle indicator; and
   an actuation pin extending outwardly from the angle leg, wherein the angle arm defines a slot dimensioned to at least partially receive the actuation pin, and the actuation pin is dimensioned to move along a length of the slot in response to movement of the angle leg relative to the housing to cause the angle arm to pivot.

10. The instrument as recited in claim 9, wherein an external surface of the housing defines the angular ruler, and the angle arm includes a tapered portion defining the angle indicator.

11. The instrument as recited in claim 10, wherein:
    the angle arm includes a main body having a generally U-shaped geometry, the slot is defined in the main body, the main body defines a recess dimensioned to at least partially receive the proximal end portion of the housing, and the tapered portion extends outwardly from an end portion of the main body; and the main body of the angle arm is pivotably attached to the proximal end portion of the housing at a retention pin.

12. The instrument as recited in claim 10, wherein the angle leg is dimensioned to extend a first length relative to the longitudinal axis, the thickness leg is dimensioned to extend a second length relative to the longitudinal axis, and the first length is greater than the second length.

13. The instrument as recited in claim 10, wherein:
the distal end portion of the housing defines a tapered engagement portion dimensioned to contact bone; and
the housing defines a passageway extending along the longitudinal axis between the tapered engagement portion and the proximal end portion, and the passageway is dimensioned to slidably receive a guide pin.

14. The instrument as recited in claim 13, wherein the angle leg tapers to a first tip portion, the thickness leg tapers to a second tip portion, and the first and second tip portions are dimensioned to contact bone on opposed opposite sides of the tapered engagement portion.

15. The instrument as recited in claim 6, wherein:
each of the angle and thickness legs includes an elongated leg body and a pair of guide rails that extend outwardly from opposite sides of the leg body;
the first and second channels extend along opposite sidewalls of the housing between the proximal and distal end portions, each of the first and second channels has a T-shaped cross-sectional geometry that is dimensioned to mate with the leg body and the pair of guide rails of respective ones of the angle and thickness legs;
the distal end portion of the housing is dimensioned to contact bone;
a terminal end of the angle leg is dimensioned to extend outwardly from the distal end portion of the housing to cause the angle arm to pivot;
a terminal end of the thickness leg is dimensioned to extend outwardly from the distal end portion of the housing to cause relative movement between the thickness indicator and the thickness ruler; and
the housing defines a passageway extending along the longitudinal axis between the proximal and distal end portions, the angle and thickness legs are spaced apart from and are on opposite sides of the passageway, and the passageway is dimensioned to slidably receive a guide pin that extends distally from the distal end portion of the housing.

16. A defect gauge instrument for evaluating a surgical site, comprising:
a housing extending along a longitudinal axis between proximal and distal end portions;
angle and thickness legs coupled to the housing, the angle and thickness legs dimensioned to contact bone adjacent the distal end portion;
an angle indicator aligned with an angular ruler;
a thickness indicator aligned with a thickness ruler;
an angle arm pivotably attached to the housing;

wherein relative movement between the angle leg and the housing causes relative movement between the angle indicator and the angular ruler;
wherein relative movement between the thickness leg and the housing causes relative movement between the thickness indicator and the thickness ruler;
wherein the housing defines the angular ruler and the angle arm defines the angle indicator such that axial movement of the angle leg relative to the longitudinal axis causes the angle indicator to pivot relative to the angular ruler; and
wherein the angle leg defines the thickness ruler and the thickness leg defines the thickness indicator such that axial movement of the thickness leg relative to the longitudinal axis causes the thickness indicator to move relative to the thickness ruler.

17. The instrument as recited in claim 16, wherein the housing defines a passageway dimensioned to slidably receive a guide pin between the angle and thickness legs.

18. A method of use for a defect gauge instrument for evaluating a surgical site, comprising:
moving a housing along a guide pin such that a distal end portion of the housing contacts bone;
measuring a retroversion angle of a defect in the bone, including causing relative movement between an angle indicator and an angular ruler in response to relative movement between an angle leg and the housing such that the angle leg contacts the bone;
measuring a thickness of the defect in the bone, including causing relative movement between a thickness indicator and a thickness ruler in response to relative movement between a thickness leg and the housing such that the thickness leg contacts the bone; and
wherein the housing extends along a longitudinal axis between a proximal end portion and the distal end portion, the housing defines a first channel extending at least partially between the proximal and distal end portions, the housing defines a second channel extending at least partially between the proximal and distal end portions, the angle leg is at least partially received in the first channel, and the thickness leg is at least partially received in the second channel.

19. The method as recited in claim 18, wherein the step of measuring the retroversion angle includes causing the angle arm to pivot in response to axial movement of the angle leg relative to the longitudinal axis of the housing, and further comprising:
rotating the housing about the guide pin from a first position to a second, different position subsequent to the steps of measuring the retroversion angle of the defect and measuring the thickness of the defect when the housing is in the first position; and
repeating the steps of measuring the retroversion angle of the defect and measuring the thickness of the defect when the housing in the second position.

20. The method as recited in claim 19, further comprising:
selecting a maximum value of the retroversion angle with respect to the first and second positions; and
selecting a maximum value of the thickness with respect to the first and second positions.

* * * * *

UNITED STATES PATENT AND TRADEMARK OFFICE
CERTIFICATE OF CORRECTION

PATENT NO. : 11,337,830 B2
APPLICATION NO. : 16/568499
DATED : May 24, 2022
INVENTOR(S) : Alexander Emmanuel Rodriguez, John David Paterson and Tyler Clevett It is certified that error appears in the above-identified patent and that said Letters Patent is hereby corrected as shown below:

In the Claims

In Claim 15, Column 11, Line 38; replace "the angle arm" with --an angle arm--

In Claim 19, Column 12, Line 44; replace "the angle arm" with --an angle arm--

Signed and Sealed this
Nineteenth Day of July, 2022

*Katherine Kelly Vidal*

Katherine Kelly Vidal
*Director of the United States Patent and Trademark Office*